US010426598B2

(12) United States Patent
Li

(10) Patent No.: US 10,426,598 B2
(45) Date of Patent: Oct. 1, 2019

(54) IMAGE PROCESSING METHOD AND SYSTEM FOR IRREGULAR OUTPUT PATTERNS

(71) Applicant: Monash University, Victoria (AU)

(72) Inventor: Wai Ho Li, Victoria (AU)

(73) Assignee: Monash University, Clayton, Victoria (AU)

( * ) Notice: Subject to any disclaimer, the term of this patent is extended or adjusted under 35 U.S.C. 154(b) by 154 days.

(21) Appl. No.: 15/124,402

(22) PCT Filed: Mar. 23, 2015

(86) PCT No.: PCT/AU2015/050123
§ 371 (c)(1),
(2) Date: Sep. 8, 2016

(87) PCT Pub. No.: WO2015/143503
PCT Pub. Date: Oct. 1, 2015

(65) Prior Publication Data
US 2017/0079770 A1    Mar. 23, 2017

(30) Foreign Application Priority Data

Mar. 25, 2014    (AU) ................. 2014901055

(51) Int. Cl.
*A61N 1/36* (2006.01)
*A61F 2/14* (2006.01)
(Continued)

(52) U.S. Cl.
CPC ............ *A61F 2/14* (2013.01); *A61N 1/36046* (2013.01); *G06K 9/00671* (2013.01);
(Continued)

(58) Field of Classification Search
CPC .................................................. A61N 1/36046
See application file for complete search history.

(56) References Cited

U.S. PATENT DOCUMENTS 7,027,874 B1    4/2006 Sawan et al.
2004/0172092 A1    9/2004 Greenberg et al.
(Continued)

FOREIGN PATENT DOCUMENTS

WO    WO 2008/140980 A1    11/2008
WO    WO 2013/029097 A2    3/2013

*Primary Examiner* — Eric D. Bertram
(74) *Attorney, Agent, or Firm* — BakerHostetler

(57) ABSTRACT

A visual image processing method is based on received spatial field information (302) from a spatial field sensor (116). A data store (804) is accessed, which contains a sensor map data structure (206) comprising a set of predefined regions (208) within a spatial field corresponding with the information received via the sensor input. Each predefined region is associated in the data structure with one or more of a set of stimuli (204) applicable to a biological visual system, and each stimulus corresponds with a visual percept (210). The spatial field information associated with each region is processed to generate stimulus control information which is applied to select, from within the sensor map data structure, stimuli from the set of stimuli for application to the biological visual system. Output stimulus signals (310) are generated, which are suitable for application to the biological visual system based upon the selected stimuli. Flexible mappings are thus provided between visual percepts, stimuli which may be applied (e.g. via a prosthetic implant) in order to generate the percepts, and associations between those stimuli and regions of the spatial field corresponding with the visual percepts.

2 Claims, 11 Drawing Sheets

(51) Int. Cl.
  *G06K 9/00* (2006.01)
  *G06T 11/00* (2006.01)
  *G06T 11/60* (2006.01)

(52) U.S. Cl.
  CPC .............. *G06T 11/00* (2013.01); *G06T 11/60* (2013.01); *A63F 2300/8082* (2013.01)

(56) References Cited

U.S. PATENT DOCUMENTS

| | | |
|---|---|---|
| 2008/0228242 A1 | 9/2008 | Fink et al. |
| 2008/0294225 A1* | 11/2008 | Roy ................... A61N 1/36046 607/54 |
| 2013/0110236 A1 | 5/2013 | Nirenberg |
| 2016/0325096 A1* | 11/2016 | Lui .................... A61N 1/36046 |

* cited by examiner

IMAGE PROCESSING METHOD AND SYSTEM FOR IRREGULAR OUTPUT PATTERNS

CROSS-REFERENCE TO RELATED APPLICATIONS

This application is the National Stage of International Patent Application No. PCT/AU2015/050123, filed Mar. 23, 2015, which claims the benefit of Australian Patent Application No. 2014901055, filed Mar. 25, 2014, the disclosures of which are incorporated herein by reference in their entireties.

FIELD OF THE INVENTION

The present invention relates to visual image processing, and particularly to processing of spatial information for rendering by systems which produce a generally irregular output image. A particular application of the invention is in image processing for prosthetic vision systems (e.g. 'bionic eyes').

BACKGROUND OF THE INVENTION

Existing cortical and retinal visual prostheses produce bionic vision by translating imagery from a head worn video camera into spatial-temporal patterns of electrical stimulation of a patient's visual pathway. The stimuli are usually delivered using multiple electrodes configured as an implanted electrode array. The resulting bionic vision consists of a spatial-temporal pattern of multiple phosphenes, experienced by the patient as visual percepts such as bright spots of light within a visual field.

In general, current limitations of technology and biology mean that the phosphene pattern has limited spatial resolution, poor dynamic range, and is also irregular. Typical properties of irregular phosphene patterns include:
- the size of individual phosphenes varies across the visual field, and the variation may not follow any mathematical or algorithmic model;
- the spatial separation between the phosphenes varies across the visual field, also without following any mathematical or algorithmic model, including the fusing of multiple phosphenes into a single phosphene or spatial configurations of fewer phosphenes;
- the shape of individual phosphenes varies across the visual field, without following any mathematical or algorithmic model;
- the intensity of individual phosphenes varies across the visual field, again without following any mathematical or algorithmic model;
- a single applied stimulus may result in multiple phosphenes, which may be spread unevenly and/or sparsely across the visual field; and
- multiple distinct stimuli may result in the same, or similar, phosphene patterns.

Many factors contribute to irregularities in phosphene patterns. Clinical trials of retinal implants, and simulations of cortical prostheses, suggest that factors such as electrode failure (dropouts), non-linear effects of the visual system (cortical magnification, visuotopic/cortical maps), irregular spreading of electrical stimulation due to implant site anatomical variations, and surgical inconsistencies in electrode placement, can all add irregularities to a patient's phosphene map. The complex processes involved are not yet fully understood, and it is likely that a number of as-yet unknown factors also contribute.

As a further result of these factors, along with a current lack of robust and accurate models of how stimuli produce phosphenes, a patient's phosphene map is not generally predictable prior to surgical implantation and electrode activation. Practical bionic vision systems therefore require a training/calibration process, in which stimuli are applied systematically in order to produce phosphenes, the location and appearance of which are reported by the patient. In this way, a mapping can be established between stimuli and phosphenes.

The phosphene mapping process may result in inaccurate estimates due to the lack of spatial and visual frames of reference that can be utilised by a vision-impaired patient and a clinician. The patient's phosphene map may therefore benefit from iterative refinement using multiple cycles of repeated measurements and adjustments to produce a better approximation of the true phosphene map of the patient. Furthermore, ongoing biological changes, and/or technical issues such as electrode failure, may require ongoing adjustment of the patient's phosphene map.

The phosphene mapping process may be regarded as an example of a more general problem of mapping regions of a 'true' visual field to a generally arbitrary and irregular output image. Other applications in which similar problems may arise include:
- Virtual Reality (VR) systems in which the output displays may be irregular due to properties of optical components (e.g. Fresnel lenses, low-cost multiple lens systems) and/or the use of multiple display panels;
- Augmented Reality (AR) systems that have irregular displays, such as spatial (projected) AR systems in which imagery may be projected onto irregular surfaces, and see-through and video pass-through AR displays that have irregular displays, or virtual content overlaid on irregular real-world surfaces; and
- Visual display systems with pixels of irregular shape, clusters of irregular pixels, or other irregularities, where it is necessary to perform graphics rendering and other processing to accommodate these irregularities.

In many of these applications, and in particular in image processing systems for prosthetic vision, it is also desirable that processing can be performed not only in a flexible manner, but also in a computationally-efficient manner. Personal and portable items, such as the processing units for prosthetic vision systems, are desirably small, light-weight, and low power consumption. Extended battery life is an extremely important characteristic in the processing unit for a visual prosthesis.

It is, accordingly, an object of the present invention to provide a flexible and efficient image processing method and system which is applicable to arbitrary and irregular output image patterns, and which may be employed in prosthetic vision processing systems, VR systems, AR systems, and other visual display and processing systems.

SUMMARY OF THE INVENTION

In one aspect, the invention provides a visual image processing method comprising:
receiving spatial field information from a spatial field sensor;
accessing a data store containing a sensor map data structure which comprises a set of predefined regions within a spatial field corresponding with the information received via the sensor input, wherein each predefined region is associated in the data structure with one or more of a set of stimuli applicable to a biological visual system, each stimulus corresponding to a visual percept;

processing spatial field information associated with each region to generate stimulus control information;

applying the stimulus control information to select, from within the sensor map data structure, stimuli from the set of stimuli for application to the biological visual system; and generating output stimulus signals for application to the biological visual system based upon the selected stimuli.

Advantageously, embodiments of the invention provide for flexible mappings between visual percepts, such as phosphenes generated within a subject's visual system, stimuli which may be applied, for example, via a prosthetic implant in order to generate the percepts, and associations between those stimuli and regions of the spatial field corresponding with the visual percepts. This decoupling of sensor maps from visual percepts provides enhanced flexibility, for example by making changes to the sensor map data structure, while enabling computationally efficient implementation when required, independent of the complexity and/or irregularity of arrangement of visual percepts.

In embodiments of the invention, the spatial field sensor comprises one or more of: a digital image sensor; a depth sensor; and an accelerometer. Other forms of spatial field sensors may also be employed.

In some embodiments, each visual percept comprises one or more phosphenes, and the sensor map data structure comprises predefined regions associating each of the one or more phosphenes with a corresponding stimulus. The predefined regions may each comprise one or more rectilinear areas. Alternatively, the predefined regions may each comprise areas of arbitrary shape. In some implementations, each predefined region comprises one or more associated weighting values.

According to some embodiments of the invention, processing of the spatial field information associated with each region comprises determining whether a property of the spatial field information within the region satisfies a threshold value, and generating stimulus control information based upon that determination.

In an exemplary embodiment, the stimulus control information is a binary value which depends upon whether or not the threshold value is satisfied. The value of the binary stimulus control information is applied to select a stimulus from the set of stimuli associated with the region, in the event that the threshold value is satisfied.

In some arrangements, the spatial field sensor is a depth sensor, and the property of the spatial field information within the region is the proximity of an object identified by the depth sensor. That is, for example, an object which is identified as being closer than a predetermined threshold distance may result in the generation of a corresponding binary control information value, which in turn results in selection of a corresponding stimulus, and generation of the associated output stimulus signals to activate a corresponding visual percept.

In other embodiments, the spatial field sensor is a digital image sensor (e.g. a digital camera, CCD array, digital video camera, or the like), and the property of the spatial field information within the region is total intensity of detected light. Alternatively, the property of the spatial field information within the region may be average intensity of detected light, which may be obtained by dividing total intensity by a measure of physical area of the region.

In some embodiments, having the advantage of good computational efficiency, the region comprises a rectilinear area, and total intensity, or average intensity, is computed using an algorithm employing integral images. More generally, the region may comprise a superposition of rectilinear areas, and total intensity, or average intensity, may be computed using an algorithm employing integral images over each rectilinear area of the superposition.

In another aspect, the invention provides a visual image processing system comprising:

a sensor input configured to receive spatial field information from an associated spatial field sensor;

a data store containing a sensor map data structure which comprises a set of predefined regions within a spatial field corresponding with the information received via the sensor input, wherein each predefined region is associated in the data structure with one or more of a set of stimuli applicable to a biological visual system, each stimulus corresponding to a visual percept;

a visual image processor configured to process spatial field information associated with each region to generate stimulus control information, and to apply the stimulus control information to select, from within the sensor map data structure, stimuli from the set of stimuli for application to the biological visual system; and a signal generator configured to receive the selected stimuli from the visual image processor, and to generate corresponding output stimulus signals for application to the biological visual system.

According to embodiments of the invention, the system further comprises an auxiliary image source, which is configured to provide spatial field information in place of information received from the spatial field sensor. Advantageously, this arrangement enables arbitrary images to be used as the basis of visual image processing, for example for testing and/or training purposes.

In particular, spatial field information provided by the auxiliary image source may comprise one or more predetermined test images.

In embodiments of the invention, the system further comprises a visualisation system configured to display a simulated image representative of the sensory experience of a subject associated with the biological visual system. In this regard, the data store may contain a percept map data structure comprising information relating to the location and appearance of visual percepts experienced by the subject in response to stimuli within the set of stimuli.

The system comprising an auxiliary image source and a visualisation system may be employed in a method of training/configuration of a prosthetic visual aid, the method comprising:

providing one or more predetermined test images via the auxiliary image source;

receiving descriptive sensory experience information from the subject (e.g. in the form of verbal feedback);

comparing the descriptive sensory experience information with the simulated image generated by the visualisation system; and adapting the percept map data structure within the data store based upon the comparison, in order to improve a correlation between the sensory experience of the subject and the simulated image representative of the sensory experience of the subject.

In another aspect, the invention provides a method of generating a sensor map data structure for use in a visual image processing system, the method comprising:

accessing a data store containing information relating to a set of stimuli applicable to the visual system of a subject, and corresponding information relating to location and appearance of visual percepts experienced by the subject in response to stimulus signals corresponding with stimuli within the set of stimuli;

selecting a stimulus from the set of stimuli, along with a corresponding visual percept;

generating a defined region corresponding with location and appearance of the selected visual percept; and storing the defined region in a sensor map data structure, wherein it is associated with the selected stimulus.

The method may comprise:

receiving spatial field information;

processing a portion of the spatial field information associated with the defined region to generate stimulus control information;

selecting, in accordance with the stimulus control information, a stimulus associated in the sensor map data structure with the defined region;

generating output stimulus signals for application to a visual system of the subject based upon the selected stimulus; and adapting the information relating to the location and appearance of visual percepts and/or the defined region in the sensor map data structure, in response to feedback received from the subject.

In yet another aspect, the invention provides a system for generating a sensor map data structure for use in visual image processing, the system comprising:

a data store containing information relating to a set of stimuli applicable to the visual system of a subject, and corresponding information relating to location and appearance of visual percepts experienced by a subject in response to stimulus signals corresponding with stimuli within the set of stimuli;

a sensor input configured to receive spatial field information from an associated spatial field sensor; and a processor configured to generate a sensor map data structure which comprises a set of defined regions within a spatial field corresponding with the information received via the sensor input, wherein each predefined region is associated in the sensor map data structure with one or more of the set of stimuli in accordance with a mapping between the location and appearance of visual percepts and the defined regions.

Further features, benefits and advantages of the invention will be apparent from the following description of embodiments, which is provided by way of example only in order to illustrate and further assist understanding of the invention. The description of embodiments is not intended to limit the scope of the invention, as summarised in the preceding statements, and defined in the claims appended hereto.

BRIEF DESCRIPTION OF THE DRAWINGS

Embodiments of the invention will now be described with reference to the accompanying drawings, in which like reference numerals refer to like features, and wherein.

DESCRIPTION OF EMBODIMENTS

Figure 1:
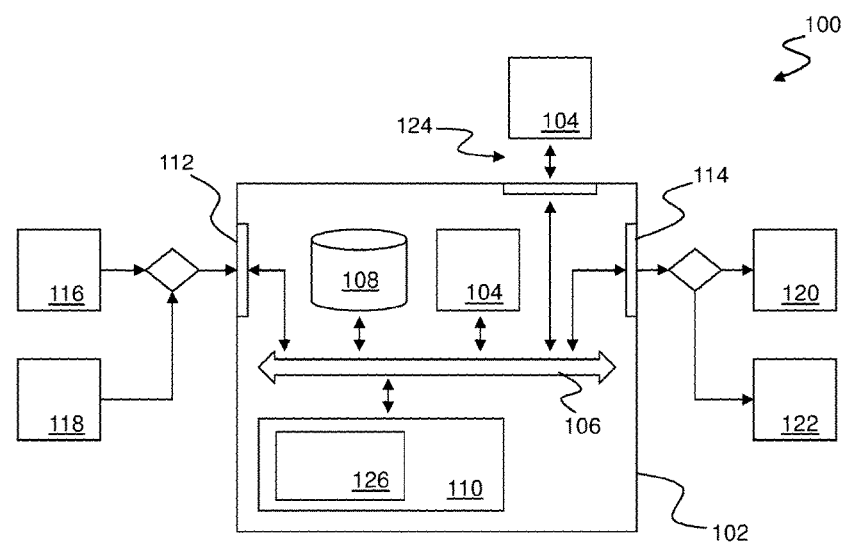
FIG. 1 is a block diagram of a visual image processing system embodying the invention.

FIG. 1 is a block diagram of a visual image processing system 100 embodying the invention. The system 100 comprises a processing unit 102, which may be a portable or wearable device carried by a patient as part of a prosthetic vision system.

The processing unit 102 includes a microprocessor 104, which is operatively associated, in use, via an address and data bus 106 with non-volatile memory 108 and volatile memory 110. In a portable device, the non-volatile memory 108 may be Read Only Memory (ROM), flash memory, or the like. If a lower level of portability is required, the non-volatile memory 108 may include a magnetic medium, such as a hard-disk drive. The volatile memory 110 is typically Random Access Memory (RAM), or similar.

The microprocessor 104 is further associated with at least one sensor input interface 112, and an output interface 114 for generation of stimuli.

Information provided to the sensor input 112 may be generated from one or more sensors 116, such as visual sensors (e.g. digital cameras or CCD arrays) and/or alternative forms of spatial sensors, such as accelerometers or depth sensors.

Additionally, training/calibration of a visual prosthetic system may be facilitated by providing for input from a test image source 118.

The output interface may be connected to an external visual prosthetic device/implant 120. This connection may be direct or indirect, e.g. via an additional signal processing/generation unit which converts stimuli signals output from the interface 114 into specific signals for application to electrodes within an implanted prosthetic device. Also shown in the system 100 is a visualization system 122, which is designed to emulate the effect of the stimuli output from the interface 114, to enable a clinician, or other operator, to visualize the processed imagery experienced by the patient.

The microprocessor 104 is also operatively associated with a further interface 124, comprising one or more user interface (UI) elements, including user inputs (e.g. switches, buttons, dials and so forth) and outputs, such as an audio interface and/or visual indicators. In some embodiments, the portable processing unit 102 may support voice control via UI elements 124.

In use, the volatile memory 110 comprises a body of program instructions 126. These program instructions are executable by the microprocessor 104, and are adapted such that the processing unit 102 is configured to perform various processing functions, and to implement the various algorithms, such as are described below, and particularly with reference to FIGS. 8 and 9.

Figure 2:
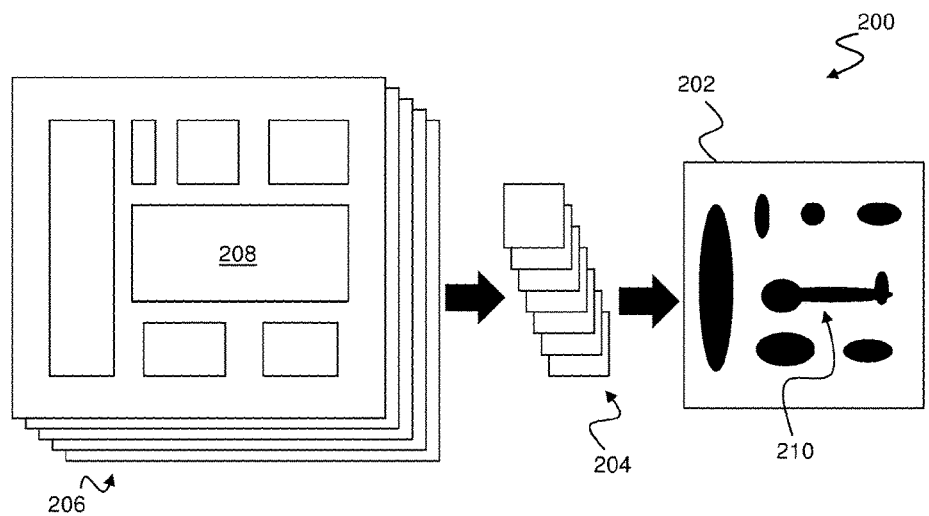
FIG. 2 is a block diagram illustrating a conceptual mapping framework embodying the invention.

FIG. 2 is a block diagram illustrating a conceptual mapping framework 200 embodying the invention. The conceptual framework 200 comprises a map of visual percepts 202, which may be, for example, phosphenes generated by the application of electrical stimuli to the visual system of a patient.

The visual percepts, e.g. 210, in the map 202 are induced, within the framework 200, either individually or in various combinations, by a set of known stimuli 204. It should be appreciated that, in the present context, the term 'stimulus' should be interpreted broadly, and refers to any signal or reference that maps to a particular visual percept, or a combination of percepts, both spatially and temporally, within the percept map 202. In the case of a prosthetic vision system, examples of stimuli include:

spatial-temporal patterns of electrical stimulation applied to the visual system using a single electrode, or multiple electrodes;

spatial-temporal patterns of electrical stimulation with tuneable parameters, such as a bi-phasic pulse train, applied using a single electrode or multiple electrodes;

combinations of spatial-temporal patterns of electrical stimulation applied to spatially adjacent electrodes in order to mimic stimulation at an intermediate location (i.e. 'virtual electrode');

spatial-temporal patterns of electrical stimulation applied using an array of electrodes in a strategic manner to produce phosphenes;

electrical signals applied to the visual system via means other than electrodes, such as Transcranial Magnetic Stimulation (TMS); and optical signals that activate cells or result in local electrical stimulation.

The framework 200 further includes one or more sensor maps 206. A sensor map is a set of mappings between the stimuli 204 and regions within spatial sensor data, such as a region of pixels in a digital image, e.g. a rectangular region 208. A region within a sensor map 206 may be defined as a spatial area, or a set of areas in a single sensor, or multiple sensors. Mappings in sensor maps may relate to:

one stimulus to a region occupying a single area in the sensor data;

one stimulus to a region occupying multiple areas in the sensor data;

one stimulus to a region occupying multiple areas across the sensor data from different sensors; and one stimulus to a region as defined in any of the above, with weighting values applied to each sensor data element within the region.

Figure 3:
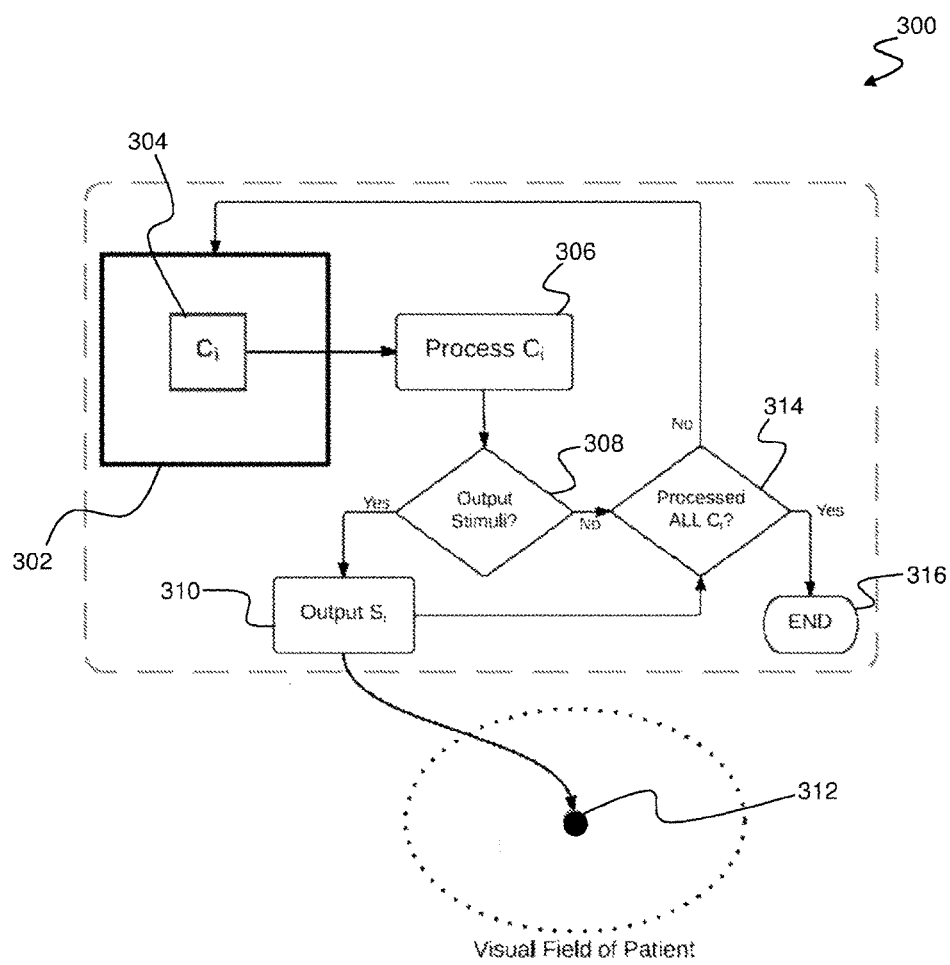
FIG. 3 is a high-level schematic diagram illustrating an image processing system based on the framework of FIG. 2.

FIG. 3 is a high-level schematic diagram illustrating an image processing system based on the framework 200 of FIG. 2. The image processing system 300 receives sensor data 302, for example, a rectangular array of pixel data corresponding with a single frame captured by a video camera.

A predefined region 304 of the sensor data 302 is selected from the current sensor map for processing 306. In general, the processing 306 is adapted to determine whether or not a stimulus associated with the region 304 should be generated. A decision 308 is made based upon the output of the processing 306. If required, a stimulus associated with the region 304, and determined by the mappings in the framework 200, is output 310. This results in the generation of the corresponding visual percept, such as phosphene 312.

The system then determines 314 whether all regions of the current sensor map have been processed. If not, a new region of the sensor data is selected, and processed 306. Once all regions have been processed, the processing of the sensor data 302 terminates 316.

Subsequently, new sensor data 302 will be received, e.g. a further frame of video data. The image processing system 300 then recommences processing, starting with the first region of the current sensor map.

Figure 4:
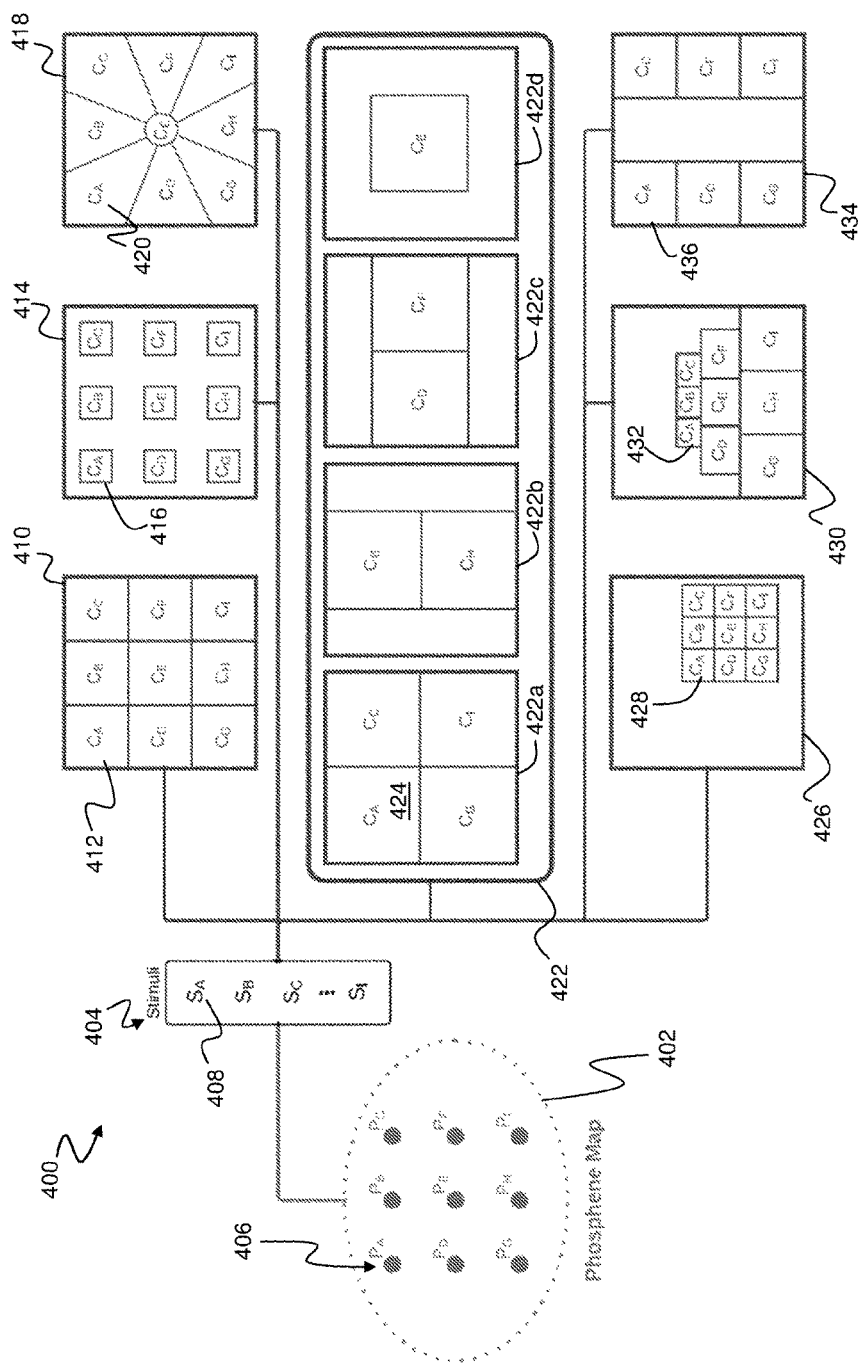
FIG. 4 illustrates exemplary sensor maps designed for a simple regular phosphene map.
Figure 5:
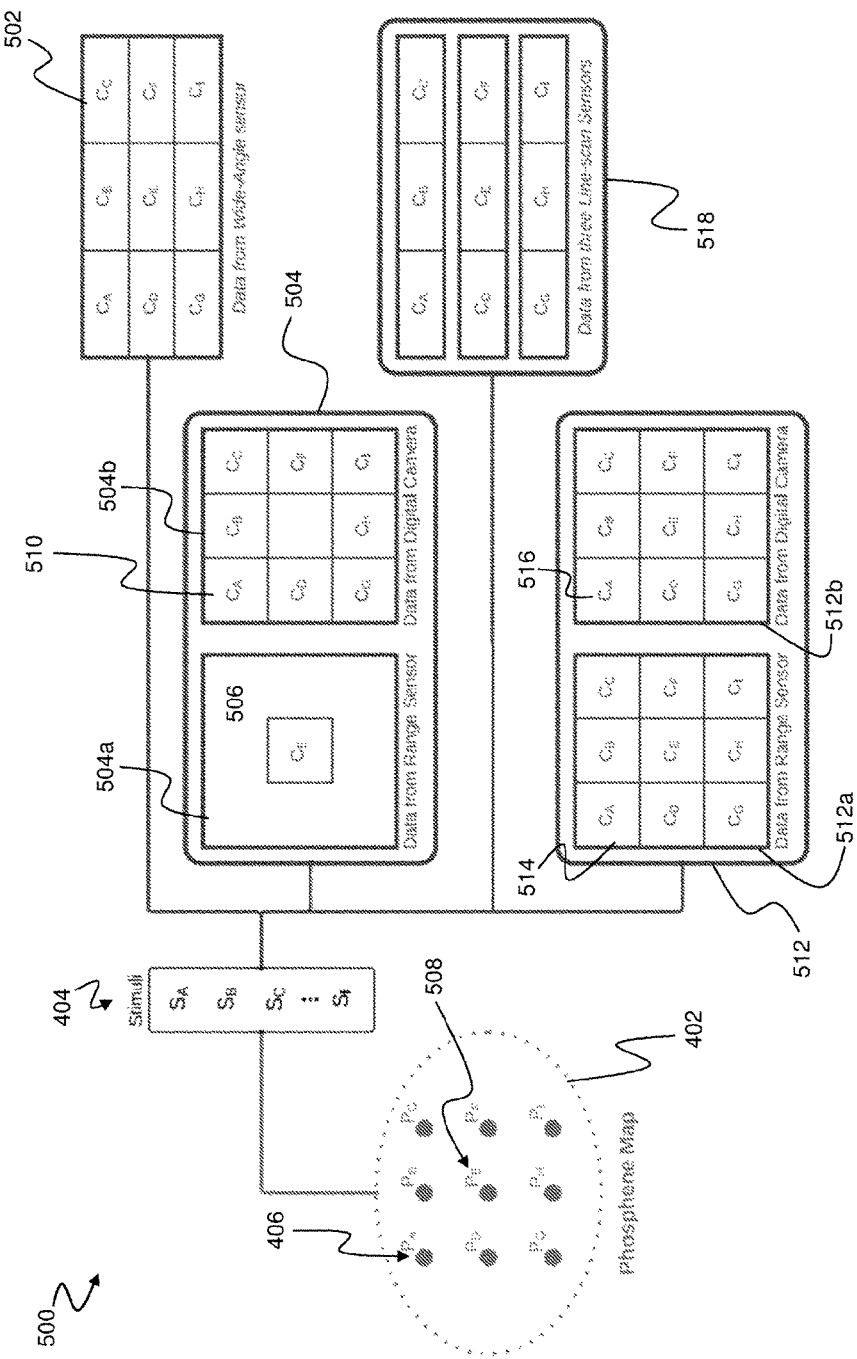
FIG. 5 illustrates exemplary sensor maps designed for different sensor configurations.
Figure 6:
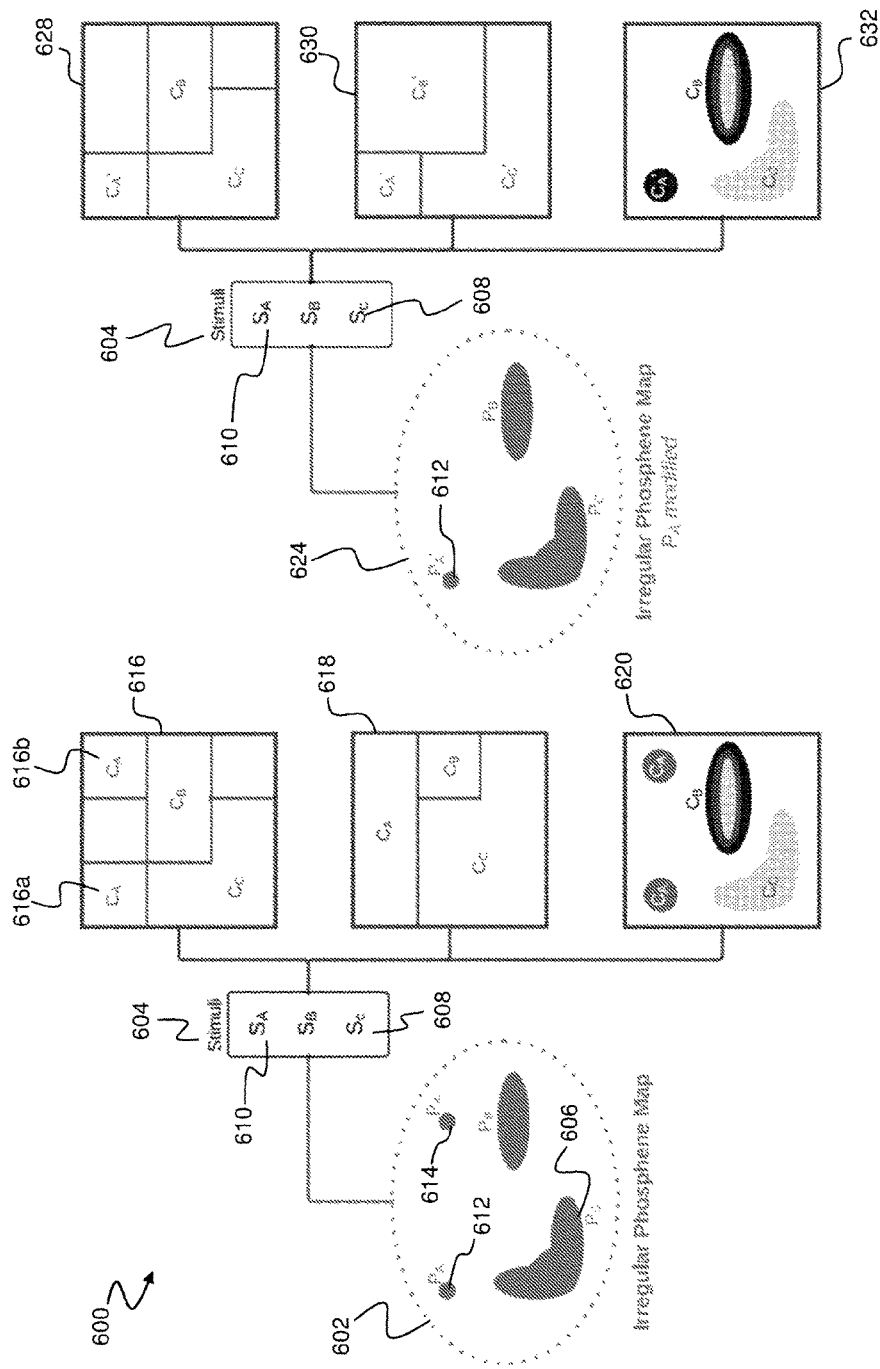
FIGS. 6(a) and 6(b) illustrate exemplary sensor maps designed for irregular phosphene maps.

A benefit of embodiments of the invention is the ability to adapt the sensor maps 206 to provide different forms of image processing independently of the mapping between stimuli 204 and visual percepts 202. FIGS. 4, 5 and 6 show a number of exemplary sensor maps illustrating the power and flexibility of the conceptual mapping framework 200 embodying the invention.

FIG. 4 shows a number of exemplary sensor maps 400 designed for use with a simple regular phosphene map 402. Although a regular phosphene map 402 is unlikely to be encountered in a practical environment, these examples serve to illustrate a number of concepts employed in embodiments of the invention. A set of stimuli 404 is associated with the phosphene map 402. In this simple illustrative example, it is assumed that each phosphene, e.g. 406, within the map 402 may be activated by selection of a corresponding one, e.g. 408, of the stimuli 404. In the examples shown in FIG. 4, it is assumed that each sensor map corresponds with visual image data, e.g. the output of a digital video camera.

A first sensor map 410 comprises a regular array of regions, e.g. 412, each of which comprises a substantially equal area of the overall image frame. The regions collectively cover the entire sensor area. The sensor data within each region is processed to determine whether or not to activate the relevant stimulus in order to generate a corresponding phosphene. For example, processing of region 412 determines whether or not to generate stimulus 408, in order to activate phosphene 406. This type of sensor map can be used in image processing approaches such as area-based thresholding or averaging, in which the input sensor data is simply downsampled and quantised to produce the output stimuli.

A second sensor map 414 also comprises a regular array of regions, e.g. 416, however these no longer collectively cover the entire sensor area. In this case, the gaps between the regions within the sensor map 414 effectively constitute 'blind spots', however the benefit is that processing of the regions, e.g. 416, may be more sensitive to changes within the image data covered by the regions of the map 414. Patient preference may be a factor in selection of a sensor map such as the map 414, and may be influenced by the fact that the regions, e.g. 416, correspond more closely with the site and location of the resulting phosphenes, e.g. 406.

A third sensor map 418 comprises regions, e.g. 420, of a different size and shape. Smaller regions correspond with a greater sensitivity to changes in the image data within the region. Accordingly, the map 418 may be suitable for fish-eye cameras and other wide-angle sensors that have higher sensing resolution towards the centre of the sensor. The map 418 allows the detection of more detailed features in the centre of the sensor data, while the radiating regions may be useful for navigational tasks in which converging straight lines are a common occurrence.

A fourth sensor map 422 comprises a number of overlapping regions which, for clarity and convenience, are shown as four sub-maps 422a, 422b, 422c, 422d. According to the map 422, a region 424 corresponding with the upper left quadrant of the sensor data is mapped to the phosphene 406. However, this region also overlaps with other regions, as shown in the sub maps 422b, 422c, 422d. Overlapping regions are allowable in the framework 200, and may be useful for image processing algorithms that require especially adjacent information. For example, this may be useful when performing a Laplacian edge detection. Larger regions may also be useful for feature detection and description using methods such as SIFT.

A fifth sensor map 426 comprises regions, e.g. 428, which collectively cover a smaller sub region of the total sensor data. This type of sensor map enables virtual pan and zoom operations to be performed. In effect, processing attention is concentrated on a specific sub-region of the overall sensor data. Notably, since the sensor map may be modified or replaced independently of the set of stimuli 404 and of the phosphene map 402, it is possible to provide a user with a controllable pan and zoom operation, for example, using a joystick or similar UI elements, via the interface 124.

A sixth sensor map 430 approximates an affine warp (planar homography). The map 430 comprises a set of regions, e.g. 432, which effectively 'recede' into the frame. This may be useful when performing tasks on planar surfaces, such as the detection of obstacles on a ground plane during navigation. As another example, if the sensor map 430 is employed when dealing with objects on a surface, such as a table, it effectively converts a perspective view of the surface to a bird's eye view.

A seventh sensor map 434 is an incomplete map, in the sense that the defined regions, e.g. 436, do not result in mappings of all of the stimuli 404 to regions of the sensor data. This is a valid sensor map within the framework 200, since it is not mandatory to have all valid stimuli mapped to regions of the sensor map. The absence of mappings means that certain stimuli cannot be produced by the image processing system, and that there is a 'blind region' running vertically through the sensor data. Applications of incomplete sensor maps include limiting the amount of electrical stimulation applied to a patient via implanted electrodes, providing image processing modes which direct attention towards specific parts of the visual field, e.g. peripheral vision, as well as a tool for use during training/calibration of a prosthetic system.

FIG. 5 illustrates further exemplary sensor maps, again based on a simple regular phosphene map 402 and corresponding set of stimuli 404. The sensor maps shown in FIG. 5 are designed for different types of sensor configuration.

A sensor map 502, for example, is designed for use where the sensor provides data corresponding with an aspect ratio different from that of the phosphene map 402. In this case, the sensor map 502 may correspond to sensor data received from a wide angle camera.

A further sensor map 504 applies to a configuration in which two different types of sensor are provided. In this case, a map 504a is applied to data received from a range sensor, while a map 504b is applied to data received from a digital video camera. According to the map 504, information at the periphery of the visual field, e.g. within region 510, is obtained by processing the digital camera sensor data, resulting in stimuli activating peripheral phosphenes, e.g. 406. However, a central region 506 of the visual field is processed based upon data obtained from a range sensor. The stimuli associated with a central phosphene 508 are generated on the basis of this processing, and, for example, may activate the phosphene 508 when an obstacle is closer than a threshold distance based upon a range data within the region 506. A visual data processing algorithm, such as an edge detection algorithm, may be employed within the peripheral regions defined in the map 504b.

The sensor map 512 again includes two separate maps 512a, 512b corresponding with sensor data received from a range sensor and from a digital camera respectively. In this case, both maps 512a. 512b comprise regions, e.g. 514, 516, corresponding with the same stimulus from the set of stimuli 404, and thus the same phosphene, e.g. 406. In this case, the processing performed to determine the activation of stimuli may employ a combination of both range and image information for each phosphene. This type of mapping may also be useful for image processing algorithms that operate on multiple streams of video data, such as dense stereo disparity and 3D reconstruction algorithms.

Finally, in FIG. 5, a sensor map 518 has regions spread across three different sensors. For example, each row of regions may correspond with a line-scan sensor which produces one-dimensional intensity or range data. The map 518 allows image processing to be performed on data from all three sensors. This type of sensor map is useful for configurations in which multiple sensors are geometrically configured to sense different portions of a scene, and the map effectively 'stitches' readings from multiple sensors into a single spatial view of the environment.

FIG. 6 illustrates exemplary sensor maps configured for use with irregular phosphene maps 602, 624. In both cases, a set of stimuli 604 is associated with activation of the phospenes in the phosphene maps 602, 624. For example, one stimulus 608 is associated with activation of the irregularly shaped phosphene 606. In FIG. 6(a), a stimulus 610 is associated with activation of a pair of phosphenes 612, 614, while in FIG. 6(b) the stimulus 610 is associated with activation of a single phosphene 626.

Considering firstly the phosphene map 602, a first sensor map 616 has a similar spatial layout to the irregular phosphene map 602, but uses regions with rectilinear areas. In particular, a region corresponding with the phosphenes 612, 614 is associated with two areas 616a, 616b that mimic the layout of the two phosphenes produced by stimulus 610. The use of rectilinear areas has the advantage of lower and more consistent computational cost for certain image processing algorithms.

A second sensor map 618 is an alternative to the sensor map 616 which occupies the entire sensor data area while retaining a similar spatial configuration to the irregular phosphene map 602. Multiple sensor maps can be designed for the same irregular phosphene pattern, and the choice between sensor maps can be made based on patient preference and other considerations, such as image processing computational requirements.

A third sensor map 620 is a weighted map, in which locations within each region have an additional value, i.e. a weight, associated with them. Areas, or individual pixels within each area, may carry different weightings. A higher weighting may imply that the state of an associated item of sensor data (e.g. a pixel in a digital image frame) has a greater influence on the decision to output a selected stimulus. For example, a simple binary weighting scheme can be used to mask away unwanted areas in a region that should be ignored by an image processing system, by setting the weights within the mask region to zero. Alternatively, weights can be used as values that represent the level of uncertainty in sensor data, or used to indicate how reliably a phosphene can be produced using the stimuli associated with a region. Weights can also be used to perform various weight-based computer vision and image processing algorithms, such as weighted averaging, or the construction of weighted histograms of gradient orientations.

Turning now to FIG. 6(b) the irregular phosphene map 624, may be regarded as a modified version of the phosphene map 602, in which one of the two phosphenes, i.e. phosphene 614, activated by the stimulus 608 is now absent. In a practical scenario, a change of this kind may result from a new measurement of a patient's phosphene map, or changes in the electrode interface with a patient's visual system. An advantage of embodiments of the present invention is that it is a relatively simple matter to update sensor maps to account for such changes in percept maps.

Accordingly, in a modified first sensor map 628 the two-area region has been modified by removing the area 616b, leaving only the area 616a.

Sensor map 630 retains the property of sensor map 618 that the entire image area is covered, as well as continuing to reflect the spatial layout of the phosphene map 624.

The weighted sensor map 632 differs from the map 620 in that the area corresponding with the absent phosphene 614 has been removed, and the weighting of the area corresponding with the remaining phosphene 612 has been adjusted. For example, the same changes which have resulted in the loss of phosphene 614 may have reduced the reliability of activating the phosphene 612 via stimulus 608. Applying a lower weighting represents an increase in the difficulty of activating the phosphene 612 when using image processing systems that perform weighted operations, such as weighted averaging followed by thresholding or quantisation. The increased difficulty of phosphene production results from a relative increase in the threshold for applying the stimulus 608 in comparison to the other stimuli within the set 604.

Figure 7A:
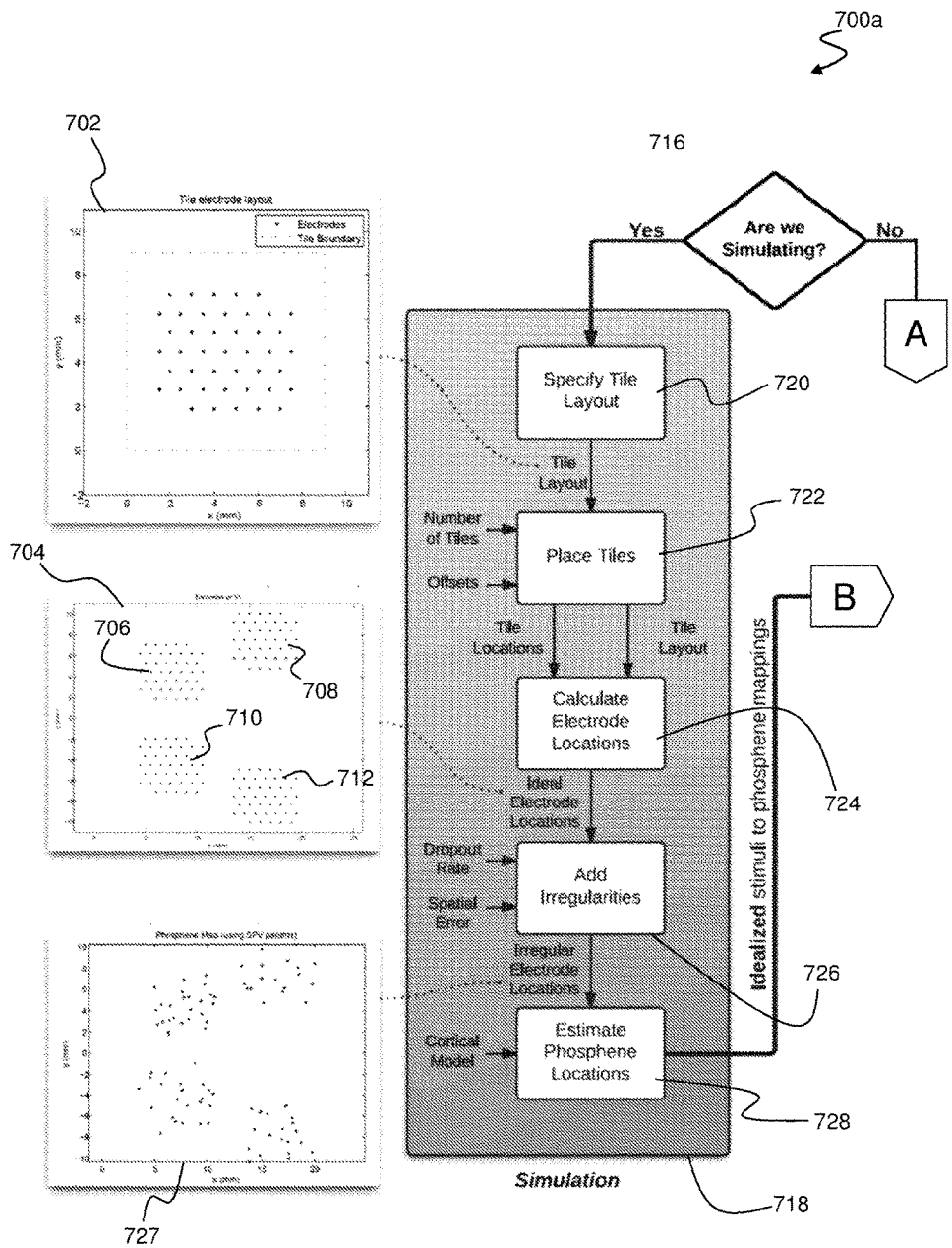
FIGS. 7A and 7B together provide a schematic diagram of a system for simulation and generation of patient data embodying the invention.
Figure 7B:
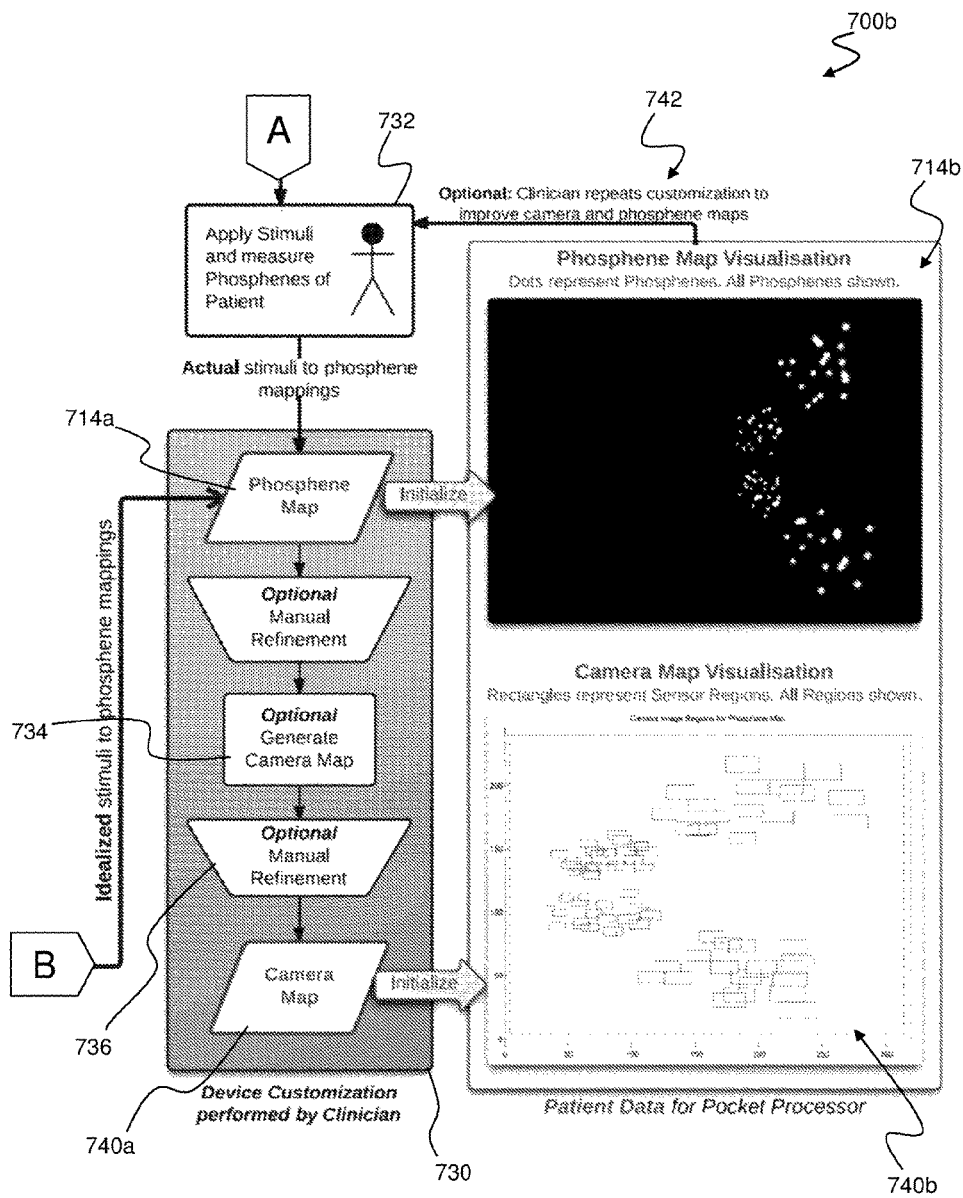

FIGS. 7A and 7B together provide a schematic diagram of a system 700a, 700b (hereafter collectively 700) for the simulation and generation of patient data embodying the invention. The purpose of the system 700 is to identify stimuli for inclusion in the stimulus set 204, to determine corresponding phosphenes for inclusion in the visual percepts map 202, and to generate one or more corresponding sensor maps 206.

In the exemplary system 700, it is assumed that a number of electrode arrays are implanted within the visual cortex of a patient. Each of these arrays comprises a regular arrangement of electrodes, as indicated in the electrode layout 702. Furthermore, multiple arrays of such electrodes will generally be implanted, resulting in the exemplary map 704 of arrays in the cortical plane (flattened V1). Four such arrays are shown 706, 708, 710, 712. In practice, the regular arrays of electrodes will generally result in an irregular pattern of phosphenes that may be activated through the application of various stimuli to the electrodes, as illustrated in the phosphene map 714a and corresponding exemplary visualisation 714b.

The system 700 comprises components and corresponding methods for obtaining an estimate of the patient's phosphene map 714a, and ultimately generating one or more corresponding sensor maps.

Two mechanisms are provided for estimation of the phosphene map 714a, which may be used individually, and/or in combination, e.g. sequentially or iteratively. These two mechanisms are simulation, based on cortical modelling, and measurement, based upon testing conducted by a clinician. A selection between simulation and measurement is made at step 716.

In the case of simulation, the modules illustrated within the simulation block 718 are executed. These modules may typically be implemented as a software application, for example executing on a conventional desktop PC, Notebook, or other suitable computing device. Simulation commences with a specification of the tile layout 720, e.g. the regular array of electrodes 702. The placement of a plurality of arrays on the cortical plane is then determined by module 722, which takes as input a specification of the number of arrays to be placed, and how they are offset relative to spatial references in the visual system, e.g. cortical plane location relative to occipital pole, or retinal location relative to blind spot, or other reference relative to the type of implant. The resulting layout is input to module 724, which determines the corresponding ideal electrode locations on the cortical plane, e.g. as illustrated in the layout 704.

The module 726 is configured to perturb the ideal electrode locations output from the module 724 in order to realistically reflect real-world phosphene maps. As shown in the system 700, two causes of irregularities are identified, namely dropouts and spatial errors, and parameters such as dropout rate or spatial error variance can be provided to control the extent of irregularity introduced by the module 726. It should be noted that one or more of the modules prior to the irregularity simulation module 726 may be omitted, and in particular that predetermined ideal electrode locations may be directly input to the module 726.

As a result of the computations performed by the irregularity generator module 726, a corresponding layout of irregular electrode locations 727 is produced, and input to a module 728 which estimates corresponding phosphene locations. The module 728 uses a model of the visual system to add additional irregularities that emulate the visuotopic mapping between electrode location and the characteristics of output phosphenes. For example, the module 728 may use a monopole cortical model, together with the assumption that each electrode only produces a single phosphine when activated. This simplifying assumption gives a one-to-one mapping between stimulus and phosphene. The output of the module 728 is a simulated set of stimulus-to-phosphene mappings, and the phosphene map is generally similar to the map 714b visualised in the system block diagram 700.

In general, the objective of the simulation block 718 is not to provide a fully accurate phosphene map, since in general simulation and modelling cannot replicate all of the physical, electrical and biological factors resulting in the phosphene map of any individual patient. The goal of simulation, rather, is to provide phosphene maps that can initialise, test and exercise an image processing system embodying the invention, and/or can act as an initial estimate of a patient's phosphene map, which can then be manually refined by additional measurements conducted under the supervision of a clinician.

A clinical measurement process is illustrated in the block 730 of the system 700. Clinical measurement involves, firstly, a step 732 of systematically applying stimuli to the patient, and measuring the resulting perceived phosphenes. Initial stimuli can be based on the results of simulation 718, and the results compared with the initial simulated phosphene map 714a, with locations, shapes and sizes of phosphenes being adjusted by the clinician based upon feedback from the patient. This process can be facilitated using the processing system 100 shown in FIG. 1, by the clinician employing the test-image source 118, and comparing a description of the phosphenes as perceived by the patient with emulated phosphenes displayed via the visualisation system 122. The visualisation system 122 may be integrated with the patient data generation system 700, such that the clinician may be able to modify the phosphene map 714a by interactively moving, resizing and/or reshaping phosphenes shown in the visualisation 714b, as well as adding or deleting phosphenes, in accordance with feedback provided by the patient.

Once a satisfactory phosphene map has been obtained, this is input to module 734 which is configured to generate one or more corresponding sensor maps. A variety of different automated algorithms may be employed to facilitate the generation of sensor maps, one example of which is shown in Appendix A, in the form of MATLAB code. This exemplary algorithm generates a single rectilinear region of a sensor map corresponding with each phosphene in the phosphene map 714a, parameterised by a 'bounding box' defining the region of interest within the sensor data within which all phosphene regions should be placed, and a scaling factor determining the relative size of each region in comparison to the measured phosphene size. Optionally, an automatically generated sensor map may be manually reviewed and refined, i.e. at step 736. The result is a sensor map 740a, such as the map shown in the visualisation 740b.

At this stage, the system 700 has determined a set of stimuli 204, a corresponding visual percept map 202, and at least one sensor map 206. The completed framework may be used, in combination with further test images, or with real-world input from a sensor 116, to assess the performance of the visual image processing system 100, and the process may optionally be repeated in order to iteratively improve the phosphene and sensor maps, as indicated by the module 742. Additionally, or alternatively, additional sensor maps may be generated for use with the image processing system 100, such as sensor maps corresponding with different regions of interest within the input sensor data.

Furthermore, alternative or additional sensor maps may be generated using other suitable algorithms. For example, automatic tessellation and partitioning methods may be used to generate sensor maps, such as Voronoi map generation algorithms.

Figure 8:
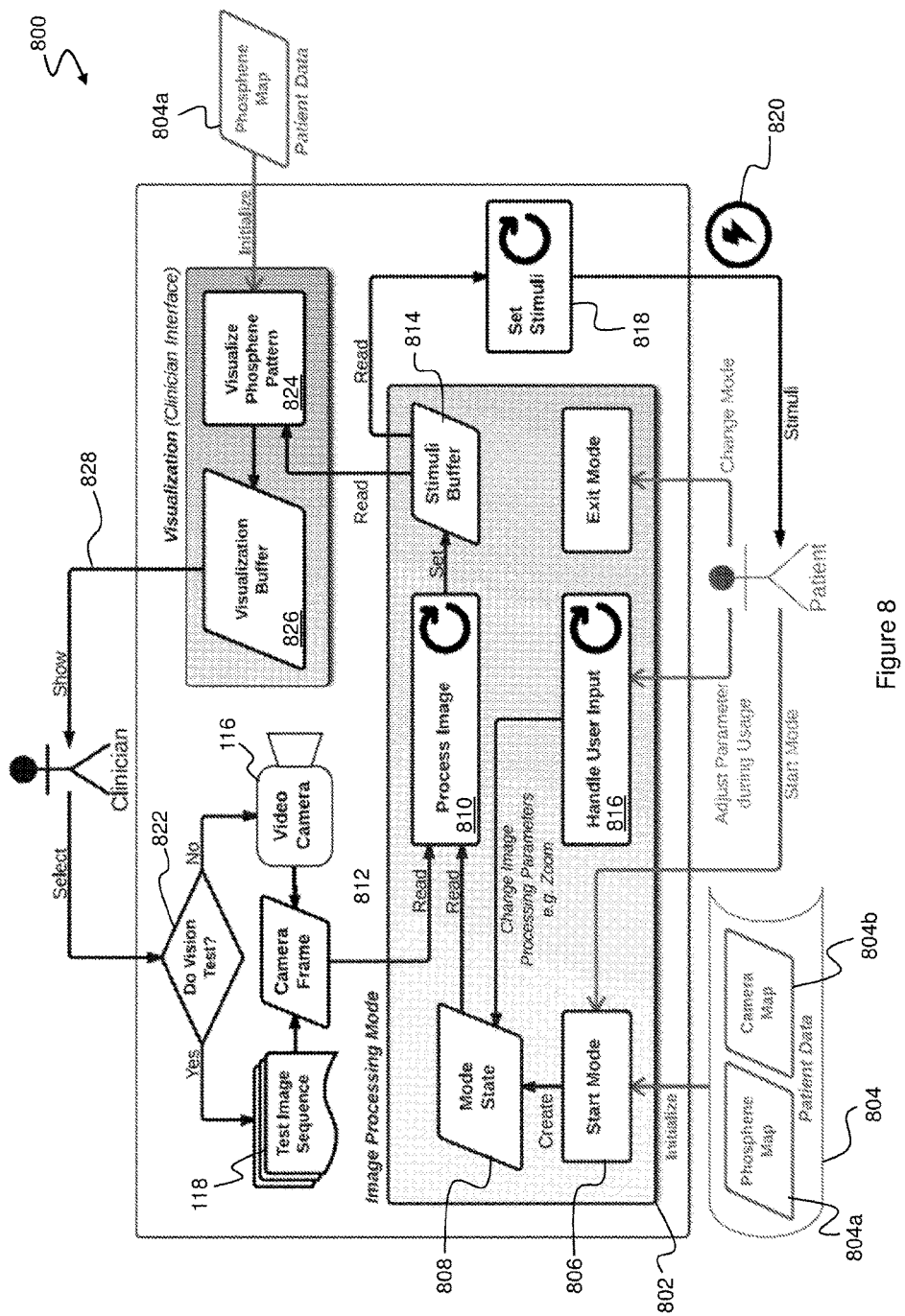
FIG. 8 is a block diagram of an image processing system architecture embodying the invention.

FIG. 8 is a block diagram of an image processing system architecture 800 embodying the invention. The architecture 800 can be implemented via software components developed and installed within the apparatus of the visual image processing system 100 as shown in FIG. 1. Depending upon requirements, different parts of the system architecture 800 are implemented within the portable processor unit 102, and within the visualisation system 122. The exemplary system architecture 800 employs input in the form of sensor data from a video camera, however image processing systems that use different and multiple sensors can also be designed, and the necessary adaptations to the system architecture 800 will be readily apparent to persons skilled in the art. For example, it is not difficult to adapt the system architecture 800 to operate using colour and depth data from an RGB-D sensor.

The image processing system architecture 800 has the following features:

- it is customisable by initialisation with the patient's phosphene map, corresponding set of stimuli, and one or more sensor maps;
- It is able to accommodate a number of different image processing modes, each of which may make use of identical or different sensor maps, including multiple sensor maps per image processing mode;
- it employs multiple parallel threads of operation, for example to capture user input, to receive and process digital video image frames, and to generate output stimuli, all of which may operate at different update rates;
- it enables a clinician to administer a vision test using test image sequences instead of video camera frames as input to any supported image processing mode; and
- it enables real-time visualisation of the system state, including Simulated Prosthetic Vision (SPV).

The system 800 is initialised by selection of an image processing mode 802, and associated patient data 804, including a phosphene map 804a and one or more sensor maps 804b. According to this embodiment, the image processing mode 802 comprises one or more executable software modules loaded from the non-volatile memory 108 of the portable processor 102, transferred to the body of instructions 126 within the memory 110, and subsequently executed by the microprocessor 104.

A 'start mode' module 806 is triggered, for example by a user input through the interface 124 (such as a button-press), which reads the patient data 804 stored, for example, in the non-volatile memory 108, and uses this information to create a mode state 808. The mode state 808 comprises a combination of processing parameters, such as thresholds, zoom strength, sensor map selection, and so forth. Processing parameters may be fixed, or may be initialised to nominal starting values and subsequently modified by user input during operation of the processing mode 802.

An image processing module 810 executes in its own thread, and is configured to repeatedly read each new camera frame 812 as it becomes available, via the input interface 112, and to process the received sensor data using a processing algorithm associated with the processing mode 802, according to any mode state parameters 808 that may be applicable. The result of the processing of each image frame by the processing module 810 is a selection of zero or more stimuli from the stimulus set 204, which are output to the stimulus buffer 814.

At all times, a further module 816 is executing in a separate thread and monitoring user input controls via the interface 124. This may include reading any dial, button, joystick or other inputs provided by the patient, and making any relevant updates to the mode state 808. For example, a dial may be used to provide a zoom function, and/or a joystick may be employed to provide a panning function, either of which may require changes to the mode state 808, such as changing image region parameters, selecting alternative sensor maps, or other parameter changes.

A 'set stimuli' module 818 is responsible for reading stimuli resulting from image processing 810 from the stimuli buffer 814, and producing a corresponding sequence of stimulus output signals 820 via the output interface 114. The 'set stimuli' module 818 may also operate in its own thread, facilitating reading and output of stimuli at a rate required by the external prosthetic device/implant apparatus 120, and independently of the camera frame generation rate and image processing rate.

It should be noted that the camera frame data 812 in the system architecture 800 may be sourced either from a test image sequence 118 or from a live video camera feed 116, and that these two input modes may be switched via a selection interface 822 by the clinician.

Stimuli which have been entered into the stimulus buffer 814 by the image processing module 810 may additionally, or alternatively, be output to a visualisation system 122. The visualisation system includes a module 824 for visualising the phosphene pattern corresponding with stimuli retrieved from the buffer 814. The phosphene pattern visualisation module 824 uses the phosphene map 804a from the patient data 804 to generate a simulated phosphene pattern based on the mapping between the stimulus set 204 and the phosphene map 804*a*. A resulting frame of simulated phosphenes is output to a visualisation buffer 826. This is in turn output 828 to a visualisation display of the visualisation system 122. The clinician is thereby able to see an approximate representation of the phosphenes perceived by the patient in response to stimuli output to the prosthetic device/implant apparatus 120.

Figure 9:
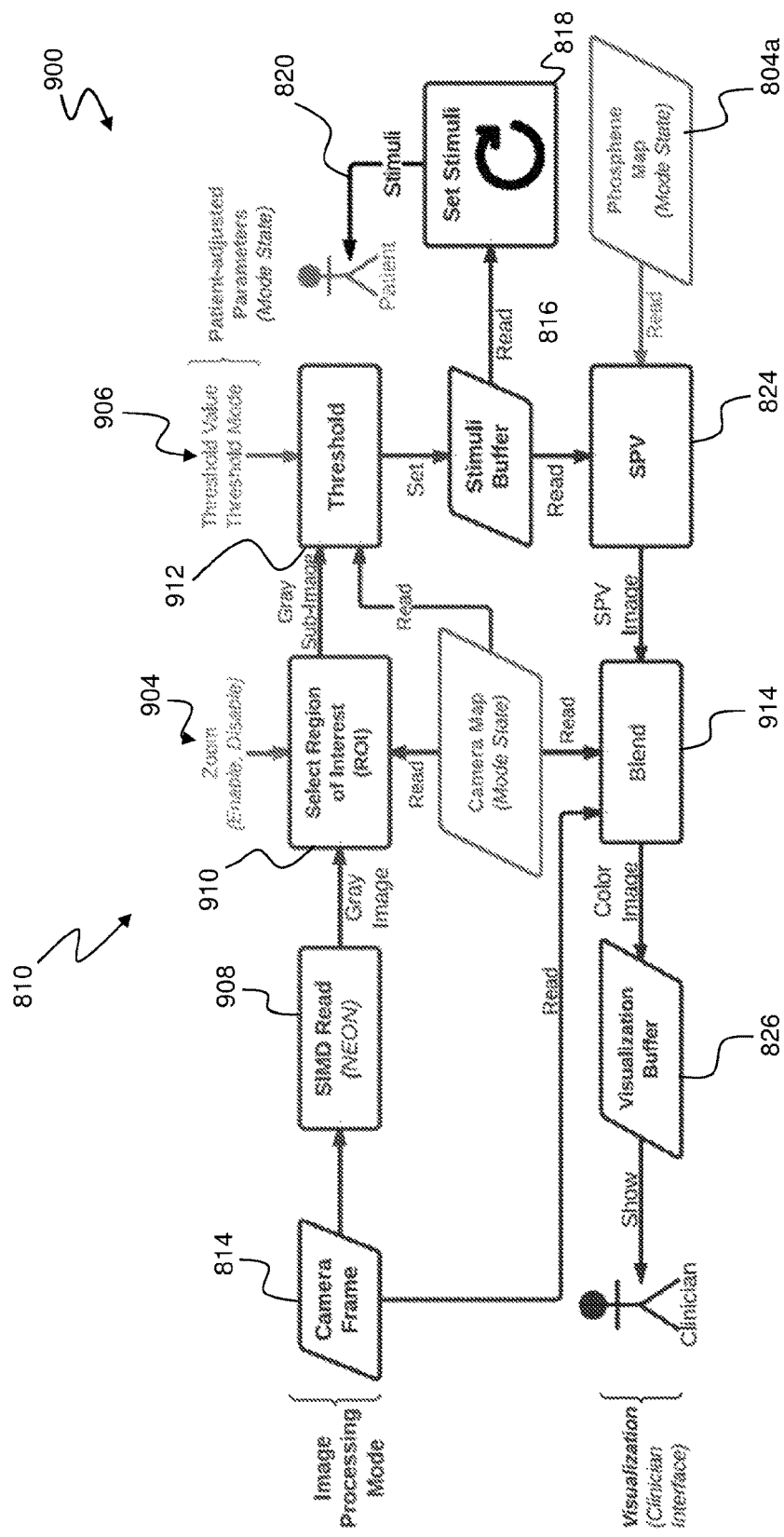
FIG. 9 is a schematic diagram of an exemplary image processing mode for the image processing system of FIG. 8.

FIG. 9 is a schematic diagram 900 illustrating functions within an exemplary image processing mode implemented within the image processing system architecture 800. The mode state 808 in this example comprises a pointer to a sensor map 902, which is selected from the maps 804*b* within the patient data 804, along with a zoom control input 904, and thresholding parameters 906.

The image processing module 810 within the processing mode 900 comprises an optimised read function 908, a region selection function 910, and a thresholding function 912. The optimised read function 908 is implemented so as to receive and transfer an image frame into memory 110 of the portable processor 102 in an efficient manner, based upon optimised memory transfer instructions and/or other efficient hardware and/or software techniques available within the hardware of the portable processor 102, and the microprocessor 104 instruction set. The optimised read function 908 may also perform basic initial image processing functions, which may also be susceptible to significant optimisation, such as the conversion of colour input to grayscale as required. The region selection function 910 employs zoom information from the mode state, e.g. a scale factor and/or an enable signal, and outputs appropriate image data to the threshold function 912. The image data made available to the threshold function 912 may comprise the complete image frame as captured by the optimised read function 908, or, when zoom is enabled, may comprise a selected sub-image, such as a central region of the full image.

The threshold function 912 accesses the camera map 902 from the mode state, along with threshold processing parameters 906. The basic object of the threshold function 912 is, for each region of the sensor map 902, to determine whether a measure of the intensity of the pixels within the region exceeds a set threshold, and if so to add a corresponding stimulus indication to the stimulus buffer 816. Further details of an exemplary threshold function 912 are provided below with reference to FIG. 11.

Figure 10:
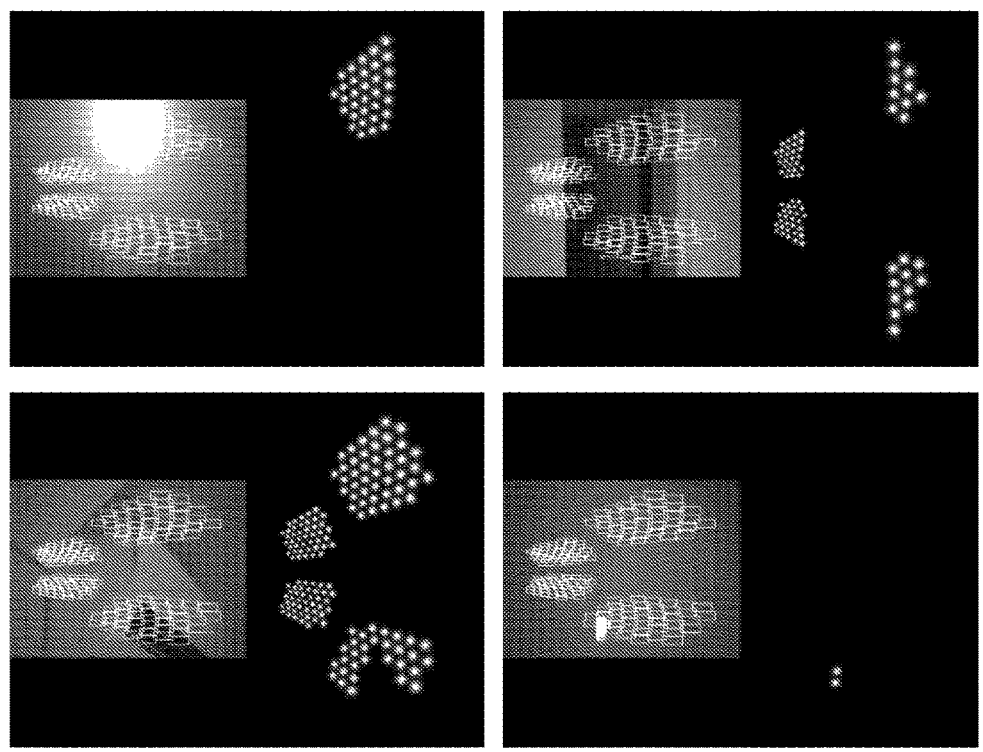
FIG. 10 shows exemplary visualised and blended images generated by the image processing mode of FIG. 9.

In accordance with the image processing system architecture 800, the resulting stimuli placed in the stimulus buffer 816 are used to generate corresponding stimuli 820 to the patient's prosthetic device/implant apparatus 120, and/or to generate Simulated Prosthetic Vision (SPV) images within a visualisation buffer 826. In the exemplary image processing mode 900, an additional 'blend' function 914 is provided, which superimposes the SPV frame with a representation of the sensor map 902 and a current camera frame 814 so that the clinician is able to view all of the relevant patient data, and compare with the actual image provided from the digital camera. By way of example, a set of the blended images transferred to the visualisation buffer 826 are shown in FIG. 10.

Figure 11:
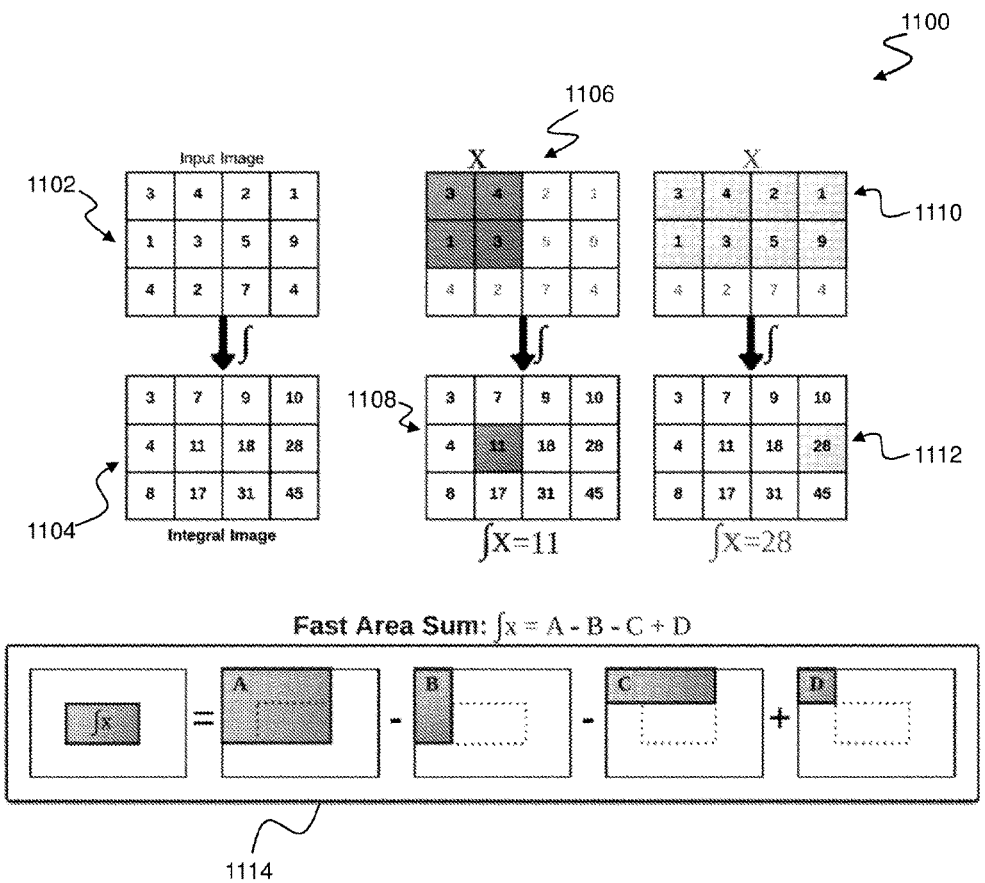
FIG. 11 illustrates integral images for use in a thresholding algorithm embodying the invention.

An exemplary thresholding algorithm will now be described with reference to FIG. 11. The thresholding algorithm is based on integral images in order to minimise total computational cost, and variance in computations cost, in the case of sensor maps comprising a number of rectilinear regions, or more complex regions that can be described as superpositions of rectilinear regions. The concept of integral images comes from the Summed Area Table concept in Computer Graphics. An advantage of integral images is that they allow rapid computations of the sum of a rectangular region of pixels. The sequence of images 1100 in FIG. 11 illustrate how an integral image can be used to calculate the sum and mean of regions in an input image.

The input image 1102 is treated as an array of pixel values, e.g. numerical values corresponding with intensity at each pixel location within the array. Each element of the corresponding integral image 1104 comprises the sum of the region of pixels to its top-left, including the current pixel value. Advantageously, the integral image 1104 can be calculated efficiently via various computational techniques, by coalescing memory accesses and summing multiple adjacent input pixels can be summed using single-instruction multiple data (SIMD) or similar optimisations.

As shown, once the integral image has been computed, the area of rectilinear regions positioned in the upper left of the pixel array 1102 can be obtained via a single read operation into the integral image array. For example, the sum of the four pixel values comprising the two-pixel square array 1106 is given by the value in the corresponding bottom right-hand element of the integral image 1108. Similarly, the sum of the four-by-two-pixel array 1110 can be obtained by reading the value in the corresponding bottom right-hand element of the integral image 1112. As shown 1114, the total of the pixel values in any arbitrary rectilinear region X can be obtained by reading four values from the integral image, corresponding with regions A, B, C and D, and computing $X=A-B-C+D$.

The mean (average) of a region is calculated by dividing its integral sum by its pixel area. Pixel areas can be pre-computed a priori for known regions to further improve computational performance. Advantageously, the integral image only has to be calculated once for an input image in order to allow quick computation of sums and means for any rectangular region.

The exemplary threshold module 912 is able to operate in real time at greater than 30 Hz using VGA resolution camera frames as input and processes hundreds of camera map regions. This level of performance is achieved on portable computational hardware suitable for visual prostheses.

The threshold module 912 is implemented as a software object with state. The algorithm is initialised using a sensor map structure comprising two arrays (or equivalent data structures such as linked lists). A first array holds rectangular regions of the camera map. A second array stores binary flags where 'TRUE' values indicate an active entry in the sensor map.

The threshold module 912 employs a fast threshold algorithm using integral images, as described above. The inputs to the threshold algorithm are a grayscale sub-image output from the ROI selection module 910, along with a threshold value, thVal, a threshold mode thMode from the current mode state (as controlled by the user) and a pointer to stimuli buffer 816. Note that the threshold used can be a fixed value, a value based on the global mean (e.g. mean of image multiplied by a fixed factor) or automatically determined by a suitable threshold algorithm. If a thMode is used where the threshold value is determined automatically by the algorithm, the value used is returned in a corresponding variable, thValUsed.

The exemplary algorithm computes the average intensity of pixels within each active rectangular region specified in the sensor map structure, compares each average intensity value with the relevant threshold value, thVal, and, if the average intensity within the region exceeds the threshold value, looks up the stimulus corresponding with the region and adds it to the stimuli buffer 816.

The above description of an exemplary threshold algorithm assumes a simple embodiment in which each percept is either 'on' or 'off', and thus each stimulus is either present or absent, based on the result of the threshold calculation. In an alternative algorithm, each percept (e.g. phosphene) can have multiple levels of intensity. This is achieved using a thresholding method that compares with multiple threshold levels thVali and producing corresponding quantised output values. The stimuli written to the stimuli buffer 816 output can then be selected based upon the quantised phosphene intensity.

While particular embodiments and variations of the invention have been described herein, further modifications and alternatives will be apparent to persons skilled in the relevant arts. For example, the thesholding mode described above may be replaced with an alternative algorithm, such as an edge-detection algorithm, or other algorithm for obtaining and presenting meaningful spatial information based upon input from a visual image sensor, and/or any other available spatial sensors. A number of alternative algorithms are described in the applicant's earlier international application publication no. WO2013/029097, the contents of which are hereby incorporated in their entirely herein by reference.

Accordingly, the described embodiments should be understood as being provided by way of example, for the purpose of teaching the general features of the invention, but should be understood as not limiting of the scope of the invention, which is defined in the following claims.

APPENDIX A

```
1   % Generates Camera Map, which contains a mapping between
    individual
2   % stimuli (results in Phosphenes) and a rectangular pixel patch in
    camera image
3   %
4   % Author: Wai Ho Li
5   % Date: 10 April 2013
6   %
7   % function camera_map = gen_camera_map (Phos, cam_size. ROI,
    phos_scale
8   %    phos — Phosphene map. Output of gen_phos ( ) function
9   %    ROI — [x, y, w, h] region of interest to fit phosphene regions
         within
10  %    phos_scale — Isotropic scaling factor for phosphene region size
11  function camera_map = gen_camera_map (phos. ROI, phos_scale)
12      camera_map.e_num = phos.e_num;
13      camera_map.enable = phos.enable:
14      camera_map.rect = zeros (length (phos.e_num), 4);
15
16      % Phosphene centroids
17  xy = [phos.x (phos.enable), phos.y (phos.enable)];
18
19  N = length (xy); % Number of enabled electrodes
20
21  % Getting corners of rectangles surrounding phosphene
22  xy1 = xy - (repmat (phos.M (phos.enable), 1, 2) * phos_scale/2);
23  xy2 = xy + (repmat (phos.M (phos.enable), 1, 2) * phos_scale/2);
24
25  % Scaling values to between 0 and 1
26  xy_max = [max ([xy1 (: , 1); xy2 (: , 1)], max ([xy1 (: , 2); xy2
    (: , 2)]) ];
27  xy_min = [min ([xy1 (: , 1); xy2 (: , 1)], min ([xy1 (: , 2): xy2
    (: , 2)]) ];
28
29  % Allowing for padding around outer edge for 3x3 kernels
30  wh_max = max (xy2 - xy1);
31  xy_min = xy_min - wh_max;
32  xy_max = xy_max + wh_max;
33
34  xyl = (xyl - repmat (xy_min, n, 1) ) ./repmat ( (xy_max - xy min),
    n, 1;
```

APPENDIX A-continued

```
35  xy2 = (xy2 - repmat (xy_min, n, 1) ) ./repmat ( (xy_max - xy min),
    n, 1;
36
37  % Mapping to camera ROI pixel coordinates
38  xyl_cam = xy1 .* repmat (ROI (3:4) - [1,1], n, 1) + repmat (ROI
    (1:2),
    n, 1);
39  xy2_cam = xy2 .* repmat (ROI (3:4) - [1,1], n, 1) + repmat (ROI
    (1:2),
    n, 1);
40
41  camera_map.rect (phos.enable, : ) = round ( [xyl_cam . . .
42      , xy2_cam - xyl_cam + repmat ( [1, 1], n, 1)] );
43  end
```

The invention claimed is:

1. A visual image processing system comprising:
a sensor input configured to receive spatial field information from an associated spatial field sensor;
a data store containing a sensor map data structure which comprises a set of predefined regions within a spatial field corresponding with the information received via the sensor input, wherein each predefined region is associated in the data structure with one or more of a set of stimuli applicable to a biological visual system, each stimulus corresponding to a visual percept;
a visual image processor configured to process spatial field information associated with each region to generate stimulus control information, and to apply the stimulus control information to select, from within the sensor map data structure, stimuli from the set of stimuli for application to the biological visual system;
a signal generator configured to receive the selected stimuli from the visual image processor, and to generate corresponding output stimulus signals for application to the biological visual system; and
an auxiliary image source configured to provide spatial field information in place of information received from the spatial field sensor, wherein spatial field information provided by the auxiliary image source comprises one or more predetermined test images; and
a visualisation system configured to display a simulated image representative of the sensory experience of a subject associated with the biological visual system;
wherein the data store contains a percept map data structure comprising information relating to the location and appearance of visual percepts experienced by the subject in response to stimuli within the set of stimuli.

2. A method of training/configuration of a prosthetic visual aid which comprises a visual image processing system, the visual processing system comprising:
a sensor input configured to receive spatial field information from an associated spatial field sensor;
a data store containing a sensor map data structure which comprises a set of predefined regions within a spatial field corresponding with the information received via the sensor input, wherein each predefined region is associated in the data structure with one or more of a set of stimuli applicable to a biological visual system, each stimulus corresponding to a visual percept;
a visual image processor configured to process spatial field information associated with each region to generate stimulus control information, and to apply the stimulus control information to select, from within the sensor map data structure, stimuli from the set of stimuli for application to the biological visual system;

a signal generator configured to receive the selected stimuli from the visual image processor, and to generate corresponding output stimulus signals for application to the biological visual system; and an auxiliary image source configured to provide spatial field information in place of information received from the spatial field sensor, wherein spatial field information provided by the auxiliary image source comprises one or more predetermined test images; and a visualisation system configured to display a simulated image representative of the sensory experience of a subject associated with the biological visual system;

wherein the data store contains a percept map data structure comprising information relating to the location and appearance of visual percepts experienced by the subject in response to stimuli within the set of stimuli;

the method comprising:

providing one or more predetermined test images via the auxiliary image source;

receiving descriptive sensory experience information from the subject;

comparing the descriptive sensory experience information with the simulated image generated by the visualisation system; and adapting the percept map data structure within the data store based upon the comparison, in order to improve a correlation between the sensory experience of the subject and the simulated image representative of the sensory experience of the subject.

* * * * *